US010709389B2

(12) United States Patent
Pamula et al.

(10) Patent No.: US 10,709,389 B2
(45) Date of Patent: Jul. 14, 2020

(54) SYSTEM AND METHOD FOR HEART RATE DETECTION WITH MOTION ARTIFACT REDUCTION

(71) Applicants: IMEC VZW, Leuven (BE); Katholieke Universiteit Leuven, KU LEUVEN R&D, Leuven (BE)

(72) Inventors: Venkata Rajesh Pamula, Leuven (BE); Marian Verhelst, Mechelen (BE)

(73) Assignees: IMEC VZW, Leuven (BE); Katholieke Universiteit Leuven, KU LEUVEN R&D, Leuven (BE)

( * ) Notice: Subject to any disclaimer, the term of this patent is extended or adjusted under 35 U.S.C. 154(b) by 371 days.

(21) Appl. No.: 15/939,073

(22) Filed: Mar. 28, 2018

(65) Prior Publication Data
US 2018/0279958 A1   Oct. 4, 2018

(30) Foreign Application Priority Data

Mar. 28, 2017 (EP) .................................... 17163225

(51) Int. Cl.
*A61B 5/00* (2006.01)
*A61B 5/024* (2006.01)
*A61B 5/11* (2006.01)

(52) U.S. Cl.
CPC .......... *A61B 5/721* (2013.01); *A61B 5/02416* (2013.01); *A61B 5/11* (2013.01); *A61B 5/7253* (2013.01); *A61B 2562/0219* (2013.01)

(58) Field of Classification Search
CPC ....... A61B 5/721; A61B 5/02416; A61B 5/11; A61B 5/7253; A61B 2562/0219
See application file for complete search history.

(56) References Cited

U.S. PATENT DOCUMENTS

2008/0208028 A1   8/2008  Thijs et al.
2012/0143020 A1   6/2012  Bordoley et al.
(Continued)

FOREIGN PATENT DOCUMENTS

EP   3028629 A1   6/2016

OTHER PUBLICATIONS

Rhee, Sokwoo et al., "Artifact-Resistant, Power-Efficient Design of Finger-Ring Plethysmographic Sensors Part II: Prototyping and Benchmarking", Proceedings of the 22nd Annual EMBS International Conference, Jul. 23-28, 2000, Chicago, Il, pp. 2796-2799.
(Continued)

*Primary Examiner* — Raymond L Nimox
(74) *Attorney, Agent, or Firm* — McDonnell Boehnen Hulbert & Berghoff LLP

(57) ABSTRACT

Example embodiments relate to systems and methods for heart rate detection with motion artifact reduction. One embodiment includes an electronic system for heart rate detection. The electronic system includes a random sampling sensor module. The random sampling sensor module includes a first sensor circuit configured to provide nonuniform random samples below a Nyquist rate of a photoplethysmographic signal. The random sample sensor module also includes a second sensor circuit configured to provided nonuniform random samples below a Nyquist rate of a motion signal. The motion signal and the photoplethysmographic signals are sampled with an equivalent pattern. The electronic system also includes a heart rate detection module. The heart rate detection module is configured to calculate a heart rave value based on frequencies corresponding to peak powers of calculated power spectral density value sets corresponding to the photoplethysmographic signals in a frequency range of interest.

20 Claims, 5 Drawing Sheets

(56) References Cited

U.S. PATENT DOCUMENTS

| | | | | |
|---|---|---|---|---|
| 2014/0316292 | A1* | 10/2014 | McRae | A61B 5/7275 600/504 |
| 2015/0196257 | A1* | 7/2015 | Yousefi | A61B 5/024 600/324 |
| 2016/0038045 | A1* | 2/2016 | Shapiro | A61B 5/721 600/479 |
| 2016/0051158 | A1* | 2/2016 | Silva | A61B 5/721 600/479 |
| 2016/0220188 | A1* | 8/2016 | Chon | A61B 5/1455 |
| 2016/0317096 | A1* | 11/2016 | Adams | A61B 5/02438 |
| 2016/0354038 | A1* | 12/2016 | Demirtas | A61B 5/721 |
| 2016/0361021 | A1* | 12/2016 | Salehizadeh | A61B 5/0245 |

OTHER PUBLICATIONS

Romberg, Justin, "Compressive Sensing by Random Convolution", SIAM J. Imaging Sciences, vol. 2, No. 4, 2009, pp. 1098-1128.

Lomb, N.R., "Least-Squares Frequency Analysis of Unequally Spaced Data", Astrophysics and Space Science, vol. 39, 1976, pp. 447-462.

Candes, Emmanuel et al., "Sparsity and Incoherence in Compressive Sampling", Inverse Problems, vol. 23, 2007, pp. 969-985.

Candes, Emmanuel J. et al., "An Introduction to Compressive Sampling", IEEE Signal Processing Magazine, Mar. 2008, pp. 21-30.

Dixon, Anna M.R. et al., "Compressed Sensing System Considerations for ECG and EMG Wireless Biosensors", IEEE Transactions on Biomedical Circuits and Systems, vol. 6, No. 2, Apr. 2012, pp. 156-166.

Garudadri, Harinath et al., "Artifacts Mitigation in Ambulatory ECG Telemetry", Proc. IEEE Int. Conf. e-Health Networking Applications and Services, 2010, pp. 338-344.

Baheti, Pawan K. et al., "An Ulta Low Power Pulse Oximeter Sensor Based on Compressed Sensing", Body Sensor Networks, 2009. pp. 144-148.

* cited by examiner

SYSTEM AND METHOD FOR HEART RATE DETECTION WITH MOTION ARTIFACT REDUCTION

CROSS-REFERENCE TO RELATED APPLICATIONS

The present application is a non-provisional patent application claiming priority to European Patent Application No. EP 17163225.0, filed Mar. 28, 2017, the contents of which are hereby incorporated by reference.

FIELD OF THE DISCLOSURE

The present description relates generally to biosignal acquisition systems and more specifically to systems and methods for heart rate detection using motion artifact reduction techniques.

BACKGROUND

Sensors and sensor modules worn on the body to measure or monitor biosignals, such as for example electrocardiogram (ECG), or photoplethysmogram (PPG) signals, frequently suffer from artifacts caused by motion of the body, especially when the sensors are intended to operate in continuous or ambulatory mode. A key technical challenge in such application environments is overcoming motion artifacts that significantly affect the measurements when the body is moving.

Patent applications US 2008/0208028 and US 2012/0143020 describe systems for the analysis of biopotential signals in which further motion artifact reduction or motion artifact handling techniques are used.

A technique of mitigating motion artifacts in PPG acquisition systems is described in "Artifact-resistant power-efficient design of finger-ring plethysmographic sensors", by S. Rhee et al., IEEE Transactions on Biomedical Engineering, vol. 48, no. 7, pp. 795-805, Jul. 2001. The authors rely on mechanically stabilizing the LED and PD pair housed in a double ringed aluminum unit. This mechanical approach, however, is limited to PPG sensors that have a specific form factor; the ones that can be worn as a ring.

There is a motivation to improve current state of the art systems and methods for robust HR detection.

SUMMARY

The present disclosure provides an improved electronic system and method for HR detection with motion artifact reduction.

The scope of the invention is defined by the claims.

According to example embodiments, there is provided a low power, robust random subsampling PPG readout circuit for HR detection with motion artifact reduction. In some embodiments, compressive sampling (CS) enables to reduce the LED driver power consumption of the PPG readout.

There is an ever increasing interest in wearable medical devices as a reaction to the population's increased vulnerability to cardiovascular diseases (CVD) and mental disorders. Continuous monitoring of heart rate (HR) and heart rate variability (HRV) provides critical information about an individual's cardiovascular and mental health state.

PPG based continuous HR and HRV monitoring is emerging as an attractive alternative to ECG based methods. Unlike ECG PPG is a non-contact, single point biosignal measurement technique, resulting in an increased patient comfort.

According to example embodiments, a CS based PPG readout is presented, which enables reduction of relative LED driver power consumption. The ASIC also integrates a digital back-end, which performs direct feature extraction from the CS signal to estimate average HR, without requiring complex reconstruction techniques. Feature extraction is performed in the compressed domain, using a Lomb-Scargle periodogram (LSP) to extract the average heart rate and variability, without requiring complex signal reconstruction techniques. Increased robustness is achieved through digital motion artifact reduction for PPG signals, using a spectral subtraction technique.

According to example embodiments, there is provided an electronic system for heart rate detection comprising: a random sampling sensor module including a first sensor circuit configured for providing nonuniform random samples below Nyquist rate of a PPG signal; a second sensor circuit configured for providing nonuniform random samples below Nyquist rate of a motion signal, where the motion signal is sampled with the same nonuniform pattern as the PPG signal; and a heart rate detection module configured for receiving a plurality of the PPG signal nonuniform random samples and calculating a power spectral density value set based on a Lomb-Scargle periodogram of the PPG signal samples; receiving a plurality of the motion signal nonuniform random samples and calculating a power spectral density value set based on a Lomb-Scargle periodogram of the motion signal samples; normalizing the calculated PPG and motion signal power spectral density value sets; subtracting the normalized motion signal power spectral density values from the normalized PPG signal power spectral density values; renormalizing the PPG signal power spectral density value set; and calculating a heart rate value based on the frequency corresponding to a highest power peak of the calculated PPG signal power spectral density value set in a frequency range of interest.

According to example embodiments, the heart rate detection module is configured for detecting a motion signal power spectral density peak value and the frequency corresponding to that power spectral density peak value, and normalizing the PPG and the motion signal power spectral density value sets based on a value given to the value corresponding to the frequency of that power spectral density peak value. According to example embodiments, the motion signal power spectral density peak value is the highest value in a frequency range of interest.

According to example embodiments, the PPG and the motion signal power spectral density value sets are normalized by setting the value corresponding to the frequency of that power spectral density peak value to the same normalization value and adapting the rest of the values accordingly. According to example embodiments, the normalization value is one.

According to example embodiments, the heart rate detection module is configured for calculating a renormalization factor for the normalized PPG signal power spectral density value set based on the ratio between the value of the PPG power spectral density at the frequency corresponding to the detected motion signal power spectral density peak value, and the highest value of the PPG power spectral density corresponding to a different frequency.

According to example embodiments, the motion signal is a signal from an accelerometer or a gyroscope.

According to example embodiments, the first and the second sensor circuit of the random sampling sensor module are located in the same body part of a subject.

According to example embodiments, the frequency range of interest is 0.5 to 5 Hz.

There is also provided an electronic device comprising a system for heart rate detection according to any of the example embodiments herein described.

There is also provided a method for heart rate detection comprising: receiving a plurality of nonuniform random samples below Nyquist rate of a PPG signal; receiving a plurality of nonuniform random samples below Nyquist rate of a motion signal, the motion signal being sampled with the same nonuniform pattern as the PPG signal; calculating power spectral density value sets of the PPG signal and the motion signal, based on a Lomb-Scargle periodogram of the received plurality of samples; normalizing the calculated PPG and motion signal power spectral density value sets; subtracting the normalized motion signal power spectral density values from the normalized PPG signal power spectral density values; renormalizing the PPG signal power spectral density value set; detecting a frequency corresponding to the highest power peak value of the PPG signal power spectral density in a frequency range of interest; and calculating a heart rate value based on the detected frequency.

There is also provided a computer program product and a computer readable storage medium, according to example embodiments.

BRIEF DESCRIPTION OF THE DRAWINGS

The above and other aspects of the system and method according to the present description will be shown and explained with reference to the non-restrictive example embodiments described hereinafter.

DETAILED DESCRIPTION

In the following, in the description of example embodiments, various features may be grouped together in a single embodiment, figure, or description thereof for the purpose of streamlining the disclosure and aiding in the understanding of one or more of the various inventive aspects. This is however not to be interpreted as the invention requiring more features than the ones expressly recited in the main claim. Furthermore, combinations of features of different embodiments are meant to be within the scope of the disclosure, as would be clearly understood by those skilled in the art. Additionally, in other instances, well-known methods, structures and techniques have not been shown in detail in order not to obscure the conciseness of the description.

Figure 1A:
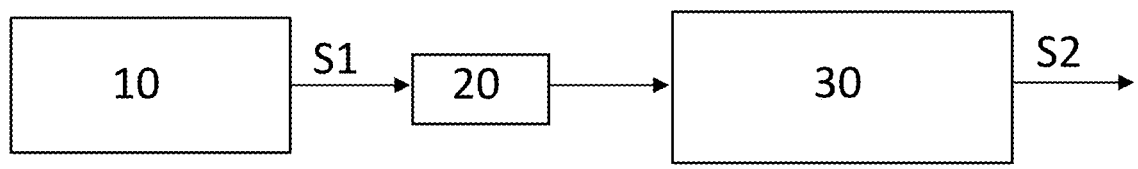
FIG. 1A shows a general block diagram of a system for heart rate detection, according to example embodiments.

FIG. 1A shows a general block diagram of an example system for heart rate detection 50 comprising a random sampling module 10 providing a randomly sampled biosignal S1, a signal conditioning module 20, and a HR detection module 30 providing information about a subject's HR and/or HRV S2. The random sampling module 10 may include a sensor that generates an analogue version of a PPG and the signal is then sampled according to current state of the art nonuniform random sampling techniques (below Nyquist sampling rate) so that a random-sampled version S1 of the sensed biosignal is provided to the next signal conditioning, transmission and/or processing stages. References for nonuniform random sampling techniques can be found in "Compressive Sensing by Random Convolution", by J. Romberg, SIAM Journal on Imaging Sciences, vol. 2, no. 4, Oct. 2009; and "Sparsity and Incoherence in Compressive Sampling", by E. Candes and J. Romberg, Inverse Prob., vol. 23, no. 3, pp. 969-985, 2007. Alternatively, the random sampling module 10 may trigger or activate a sensor according to current state of the art nonuniform random sampling techniques (below Nyquist sampling rate) so that the sensor directly generates a random sampled version S1 of the sensed biosignal. The signal conditioning module 20 may be optional and comprise an analogue to digital converter and/or any other element for conditioning of the randomly sampled signal S1 to a transmission device. The HR detection module 30 is adapted to receive information concerning the random sampled signal S1, e.g. value and time stamp when the signal was sampled, and process the received samples in order to calculate an estimation of the HR S2. According to an embodiment, the HR detection module 30 calculates an estimation of the HR based on the spectral information of the random sampled signal S1. According to example embodiments, the HR detection module 30 performs least-squares frequency analysis of the random sampled signal S1 in order to calculate an estimation of the HR. Least-squares spectral analysis (LSSA) or Lomb-Scargle periodogram is a method of estimating a frequency spectrum of unequally spaced data as described, for example, in "Least-squares Frequency Analysis of Unequally Spaced Data", N. R. Lomb, Astrophysics and Space Science 39, 447-462, 1976, in which the power spectral density (PSD) of the samples is calculated using $$P(\omega) = \frac{1}{2}\left\{\frac{\left(\sum x(t_j)\cos\omega(t_j - \tau)\right)^2}{\sum \cos^2\omega(t_j - \tau)} + \frac{\left(\sum x(t_j)\sin\omega(t_j - \tau)\right)^2}{\sum \sin^2\omega(t_j - \tau)}\right\} \quad (1)$$

$$\tan(2\omega\tau) = \frac{\sum \sin 2\omega t_j}{\sum \cos 2\omega t_j} \quad (2)$$

where $x(t_j)$ is the signal at time instant $t_j$ ($j^{th}$ sample of the signal) and $\omega$ is the frequency at which the PSD is to be estimated in rad/sec.

According to example embodiments, the HR detection module 30 calculates the PSD of a plurality of samples of the received randomly sampled signal S1 and infers the HR information from the same. According to example embodiments, an average HR over a certain predetermined time interval or window, e.g. 4 seconds, is calculated by finding the frequency (fpk) corresponding to the highest power peak in the PSD of the samples received during that time period or window and then calculating the HR, in beats per minute (bpm), as $$HR=60 \times fpk$$

An example implementation of the system for heart rate detection according to FIG. 1A is described in EP patent application 3028629 A1. Compressed sensing or compressive sampling (CS) is an emerging signal processing technique that asserts that certain signals can be recovered faithfully from far fewer number of samples or measurements. CS relies on the underlying structure of the signal which is expressed terms of its "sparsity" and the "incoherence" which is related to the sampling scheme (see for example "An Introduction to compressive sampling", E. J. Candés et al., IEEE Signal Processing Magazine, vol. 25, pp 21-30, Mar. 2008). Known state-of-the-art biosignal acquisition systems using, for example, the techniques described in "Compressed Sensing System Considerations for ECG and EMG Wireless Biosensors", A. M. R. Dixon et al., IEEE Transactions on Biomedical Circuits and Systems, vol. 6, No. 2, Apr. 2012, require, for the detection of a specific biosignal feature, such as for example the heart rate (HR), to first reconstruct an approximation of the original sampled biosignal. This means that complex signal reconstruction algorithms have to be run on the received samples in order to obtain a time domain reconstructed signal and then perform known feature extraction techniques, such as HR or heart rate variability (HRV) detection, on that time domain signal. Such reconstruction process and detection techniques are computationally intensive and hence not suited for low power sensor nodes. Typically, as described in "Artifacts Mitigation in Ambulatory ECG Telemetry", H. Garudari et al., Proc. IEEE Int. Conf. e-Health Networking Applications and Services, pp. 338-344, 2010, the reconstruction complex processing is offloaded from the sensor and performed at a separated receiver node or base station. With this technique the sensor can work with low power budget while the receiver node, which is assumed to have a better battery budget or no restrictions on power consumption, performs the computationally intensive tasks. Another example system describing a HR detector using CS techniques is described in paper "An ultra low power pulse oximeter sensor based on compressed sensing", P. K. Baheti et al., Body Sensor Networks 2009, pp 144-148, Berkeley, USA 2009.

Figure 1B:
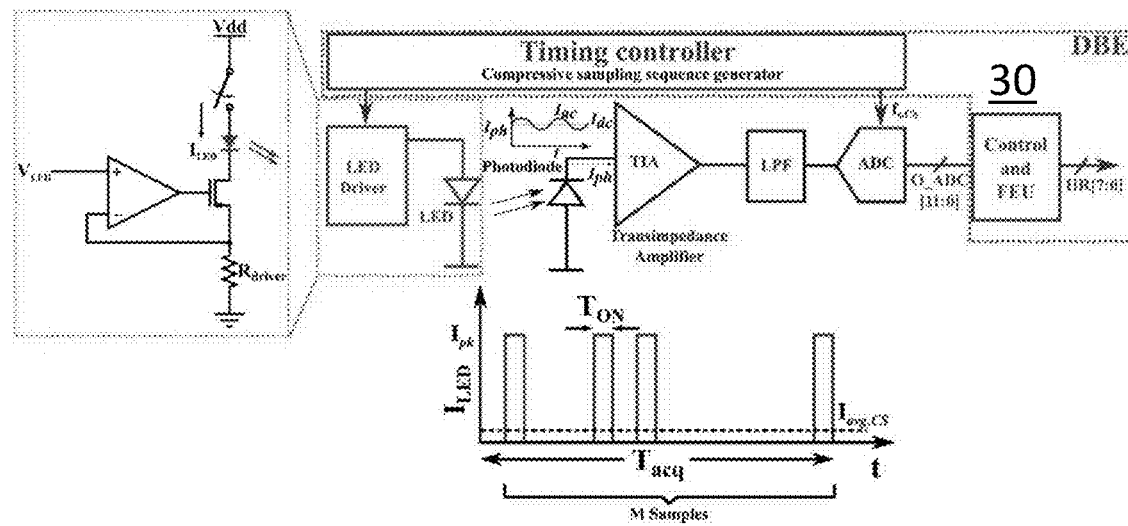
FIG. 1B shows a more detailed implementation of the CS based PPG readout circuit of FIG. 1A, according to example embodiments.

FIG. 1B shows a more detailed implementation of the CS based PPG readout circuit of FIG. 1A. The photocurrent (Iph) acquired by the PD comprises of a small AC component, which arises due to increased flow of blood during systole. The AC component rides on top of a relatively large DC component, arising due to bone and the static blood in the tissue. Since, the AC component is related to heart pulsation, its frequency is highly correlated to the HR. In a voltage mode signal processing system, this photocurrent is converted into a voltage signal through a transimpedance amplifier (TIA), which is then processed further. Compared to the conventional PPG acquisition, based on uniform sampling, CS based PPG acquisition acquires signal at an average sampling rate of fs,CS given by fs,CS=fs,N/CR, where fs,N is the uniform sampling rate.

While the acquisition of a signal in the CS framework might be relatively straightforward, recovering the signal back from the measurements, often referred to as the reconstruction process, is a very computationally intensive task. While several algorithms exist for signal recovery, with varying degrees of computational complexity, only a handful hardware implementations for the same exist. Many CS implementations reported in the literature assume the presence of a powerful base station, to which the measurement data is off-loaded over a wireless link. The reconstruction is then performed at the base station, where the power constraints are relaxed. In some embodiments, feature extraction can be performed on the sensor node directly from the CS data.

The ASIC embeds an AFE which performs a pseudorandom sub-sampled acquisition of the PPG signal and a digital back-end (DBE), which performs the HR estimation directly from the CS PPG signal. The AFE integrates a programmable gain TIA, the output of which is interfaced to a switched integrator (SI), which improves the SNR. The output of the SI is buffered and digitized through a 12-bit SAR ADC. A sub-1V bandgap reference is integrated on-chip to provide stable on-chip bias and reference signals. The DBE comprises a control unit (CU) that generates the necessary control signals used for the LED driver, AFE, and the ADC, and also the internal timing and synchronizing signals. Direct memory access (DMA) is integrated into the DBE which transfers the incoming data from the ADC into one of the data memory (DMEM) banks. The feature extraction unit (FEU), also part of the DBE, accelerates the process of LSP to enable extraction of HR directly from the CS PPG signal. The DBE is clocked through an external clock at 32 kHz. The ASIC also provides wide scale programmability both for the gain and bandwidth settings of the AFE and CR, thereby extending its utility across a wide range of photocurrent amplitudes. The first stage of the readout channel is a TIA that is interfaced to an off-chip photodiode (PD). The TIA converts the PPG signal that is acquired as a current signal at the output of the PD into a voltage signal, which is further processed by the signal processing chain in voltage domain. The TIA is realized by employing resistive feedback around a two-stage Miller compensated OTA. The output of the SI is then digitized using a 12-bit SAR ADC, which comprises of a split capacitor DAC to reduce the area requirements, with a unit capacitance. The pseudo-random sub-sampling instants of the ADC are controlled by the CU that forms part of the DBE. The digitized data, at the output of the ADC is fed into the DBE for further processing to extract the HR.

Figure 2:
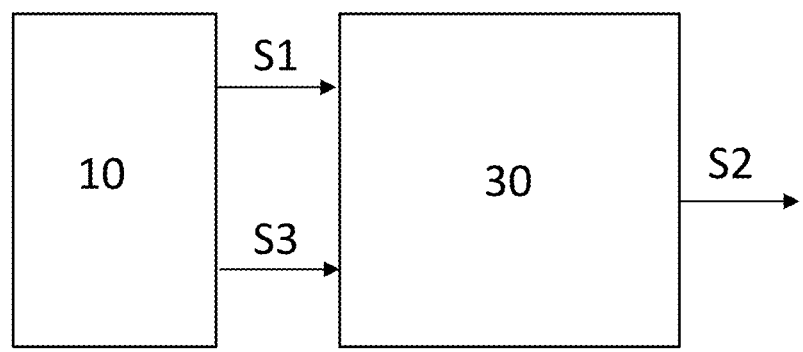
FIG. 2 shows a general block diagram of a system for heart rate detection with motion artifact reduction, according to example embodiments.

FIG. 2 shows a general block diagram of an example system 100 for heart rate detection with motion artifact reduction. The system comprises a random sampling sensor module 10 including a first sensor circuit configured for providing nonuniform random samples below Nyquist rate of a PPG signal S1; a second sensor circuit configured for providing nonuniform random samples below Nyquist rate of a motion signal S3, where the motion signal are sampled with the same nonuniform pattern as the PPG signal; and a heart rate detection module 30 configured for receiving a plurality of the PPG signal nonuniform random samples S1 and calculating a power spectral density value set based on a Lomb-Scargle periodogram of the PPG signal samples; receiving a plurality of the motion signal nonuniform random samples S3 and calculating a power spectral density value set based on a Lomb-Scargle periodogram of the motion signal samples; normalizing the calculated PPG and motion signal power spectral density value sets; subtracting the normalized motion signal power spectral density values from the normalized PPG signal power spectral density values; renormalizing the PPG signal power spectral density value set; and calculating a heart rate value S2 based on the frequency corresponding to a highest power peak of the calculated PPG signal power spectral density value set in a frequency range of interest.

According to example embodiments, the motion signal S3 is a signal from an accelerometer or a gyroscope.

According to example embodiments, the first and the second sensor circuit of the random sampling sensor module 10 are located in the same body part of the subject, such that the motion signal represents a motion artifact actually affecting the PPG sensor module.

According to example embodiments, the frequency range of interest is 0.5 to 5 Hz, representing a HR between 30 and 300 bpm.

Figure 3:
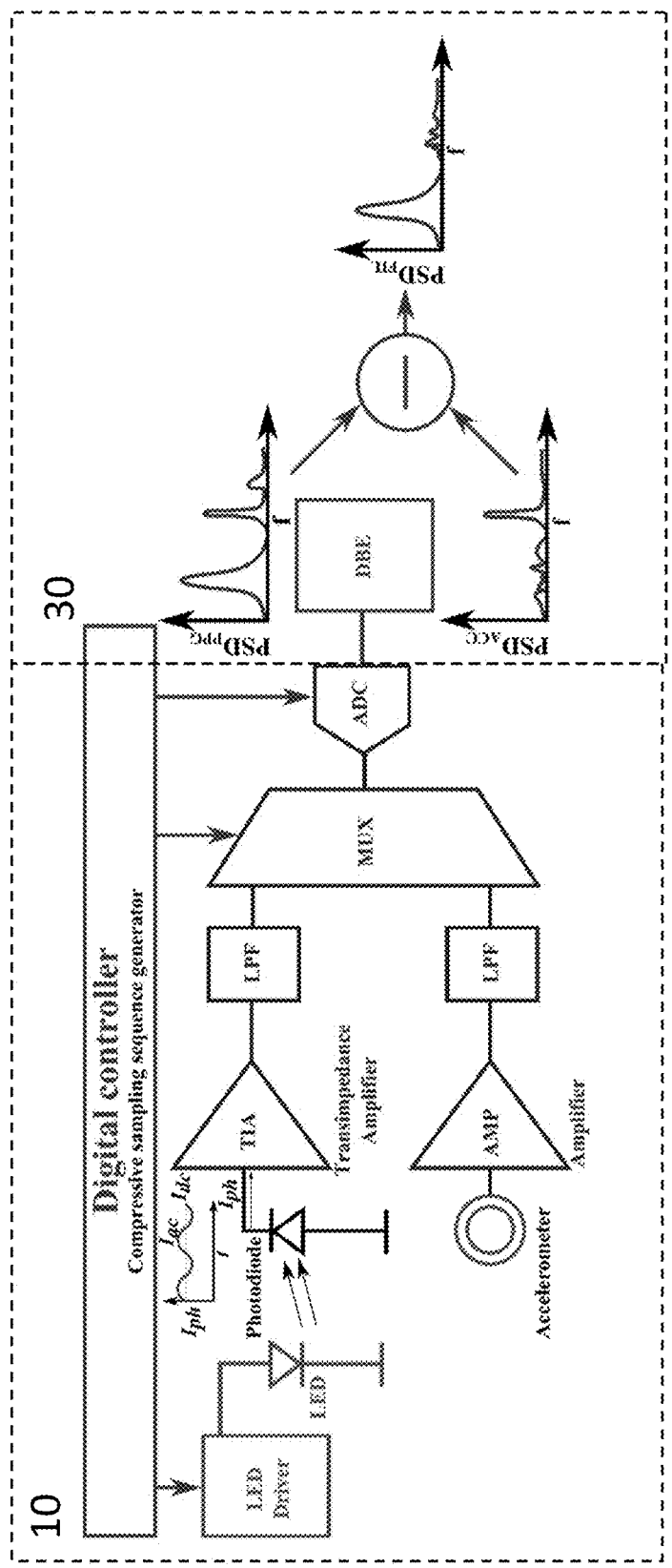
FIG. 3 shows a more detailed implementation of the system for heart rate detection with motion artifact reduction of FIG. 2, according to example embodiments.

FIG. 3 shows a more detailed implementation of the system for heart rate detection with motion artifact reduction of FIG. 2.

Figure 4:
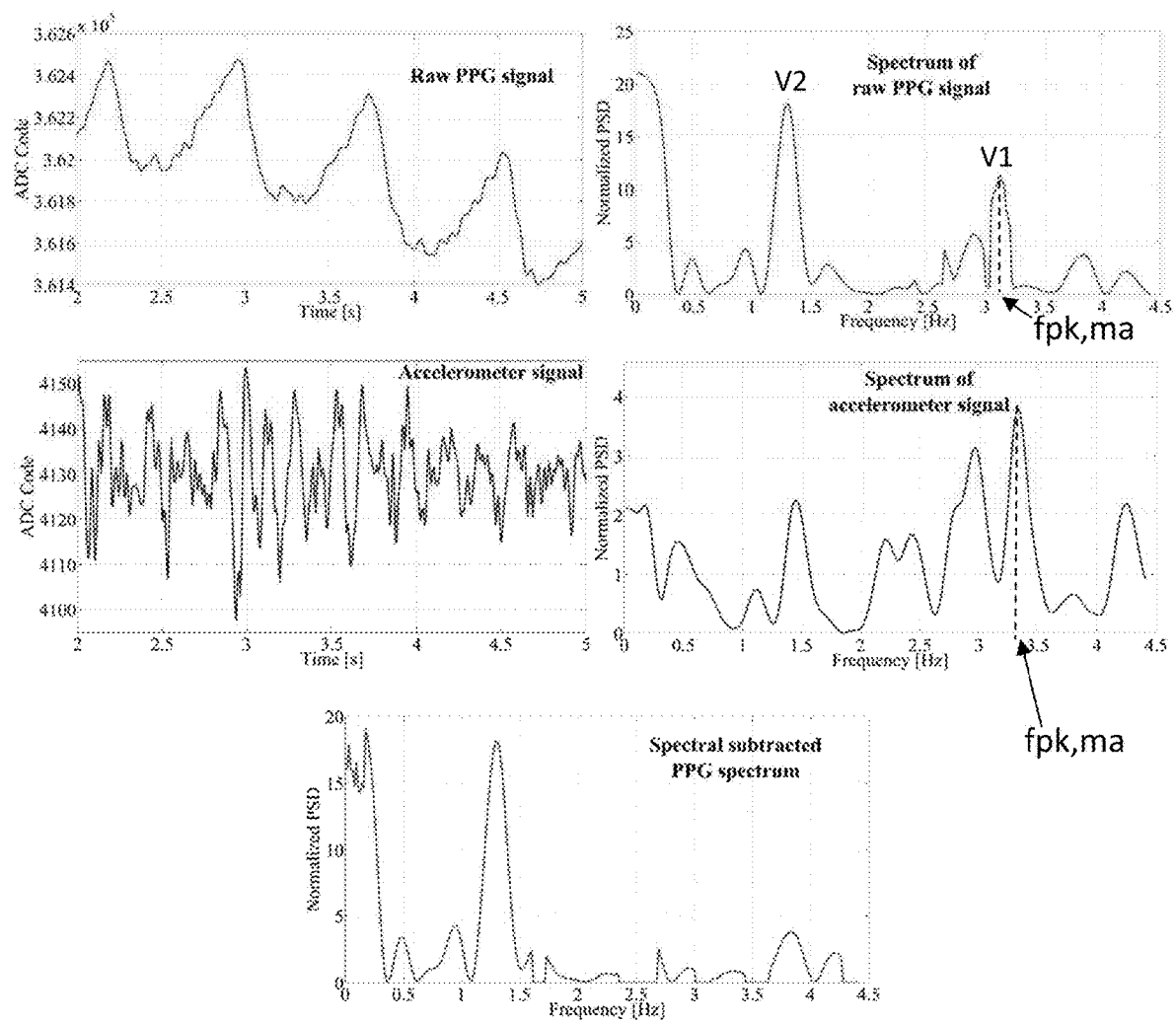
FIG. 4 shows graphs of the PPG and motion signal both in time domain and their PSD transformation and the resulting PPG power spectral density after motion artifact subtraction, according to example embodiments.

FIG. 4 shows graphs of the PPG and motion signal both in time domain and their PSD transformation and the resulting PPG power spectral density after motion artifact subtraction. According to example embodiments, the heart rate detection module 30 is configured for detecting a motion signal power spectral density peak value and the frequency fpk,ma corresponding to that power spectral density peak value, and normalizing the PPG and the motion signal power spectral density value sets based on a value given to the value corresponding to the frequency fpk,ma of that power spectral density peak value. According to example embodiments, the motion signal power spectral density peak value is the highest value in a frequency range of interest. According to example embodiments, the PPG and the motion signal power spectral density value sets are normalized by setting the value corresponding to the frequency fpk,ma of that power spectral density peak value to the same normalization value and adapting the rest of the values accordingly. According to example embodiments, the normalization value is one.

According to example embodiments, the heart rate detection module 30 is configured for calculating a renormalization factor for the normalized PPG signal power spectral density value set, based on the ratio between a first value V1 of the PPG power spectral density at the frequency fpk,ma corresponding to the detected motion signal power spectral density peak value, and a second value V2 being the highest value of the PPG power spectral density value set corresponding to the rest of frequencies of interest.

Figure 5:
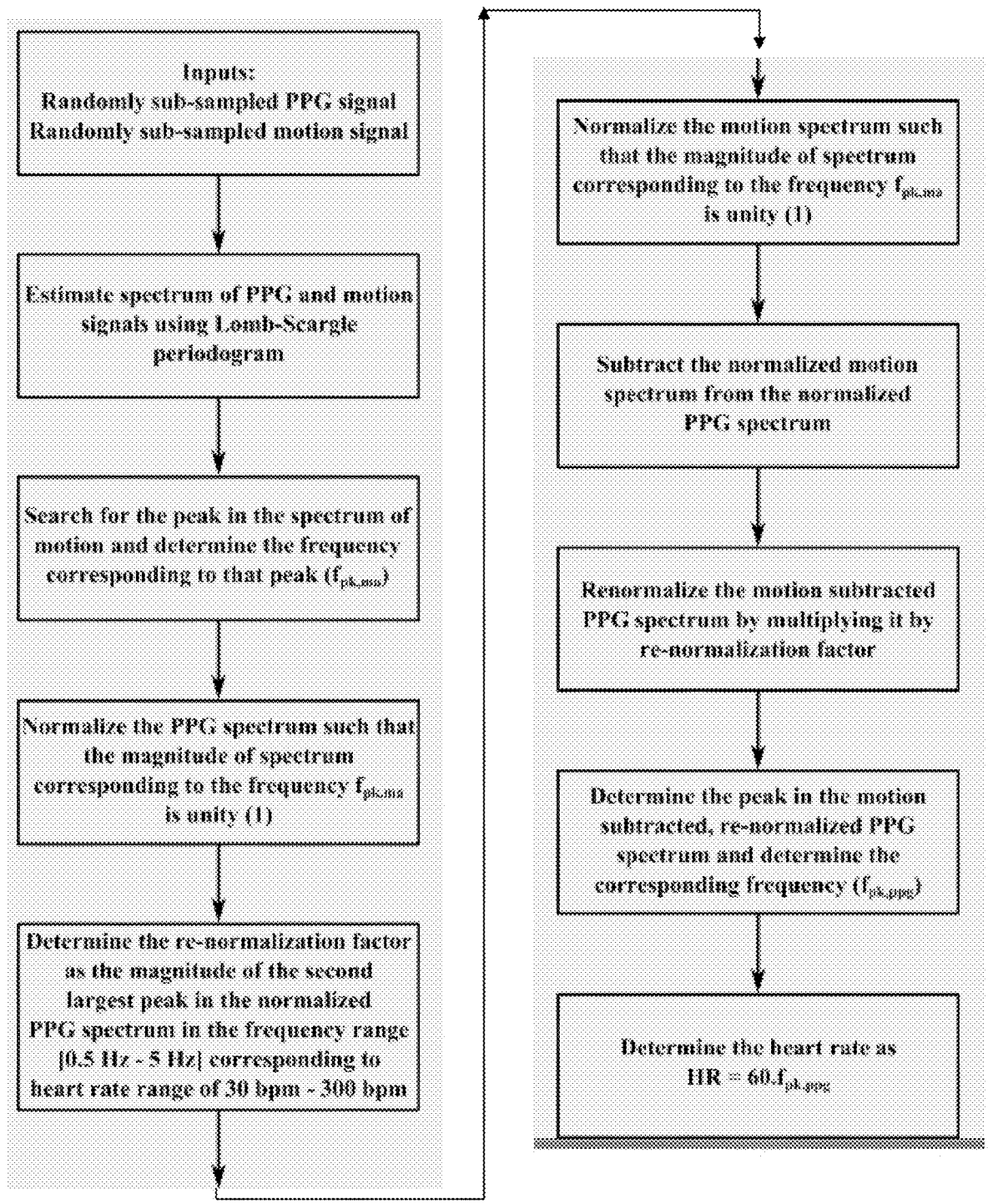
FIG. 5 shows a flow diagram of a method for calculating HR with motion artifact reduction, according to example embodiments.

FIG. 5 shows a flow diagram of a method for calculating HR with motion artifact reduction according to example embodiments.

It shall be noted that the HR detection module 30 may be implemented according to hardware and/or software state of the art techniques, comprising for example a microprocessor, microcontroller or digital signal processor that can understand and execute software program instructions. Some programmable hardware logic and memory may be specifically designed also for executing the method or parts of it, according to example embodiments.

What is claimed is:

1. An electronic system for heart rate detection comprising:
　a random sampling sensor module comprising:
　　a first sensor circuit configured to provide nonuniform random samples below a Nyquist rate of a photoplethysmographic signal; and
　　a second sensor circuit configured to provide nonuniform random samples below a Nyquist rate of a motion signal, wherein the motion signal is sampled with an equivalent nonuniform pattern as the photoplethysmographic signal; and
　a heart rate detection module configured to:
　　receive a plurality of the nonuniform random samples below the Nyquist rate of the photoplethysmographic signal;
　　calculate a power spectral density value set based on a Lomb-Scargle periodogram of the nonuniform random samples below the Nyquist rate of the photoplethysmographic signal;
　　receive a plurality of the nonuniform random samples below the Nyquist rate of the motion signal;
　　calculate a power spectral density value set based on a Lomb-Scargle periodogram of the nonuniform random samples below the Nyquist rate of the motion signal;
　　normalize the calculated power spectral density value sets corresponding to the photoplethysmographic signal and the motion signal;
　　subtract the normalized power spectral density value set corresponding to the motion signal from the normalized power spectral density value set corresponding to the photoplethysmographic signal;
　　renormalize the power spectral density value set corresponding to the photoplethysmographic signal; and
　　calculate a heart rate value based on a frequency corresponding to a highest power peak value of the calculated power spectral density value set corresponding to the photoplethysmographic signal in a frequency range of interest.

2. The electronic system for heart rate detection according to claim 1, wherein the heart rate detection module is further configured to:
　detect a motion signal power spectral density peak value and a frequency corresponding to the motion signal power spectral density peak value;
　normalize the power spectral density value set corresponding to the photoplethysmographic signal based on the motion signal power spectral density peak value; and
　normalize the power spectral density value set corresponding to the motion signal based on the motion signal power spectral density peak value.

3. The electronic system for heart rate detection according to claim 2, wherein the motion signal power spectral density peak value is a maximum value in a frequency range of interest.

4. The electronic system for heart rate detection according to claim 2, wherein the power spectral density value set corresponding to the photoplethysmographic signal and the power spectral density value set corresponding to the motion signal are normalized by setting a power spectral density value corresponding to the frequency of the motion signal power spectral density peak value to an equivalent normalization value and adapting a remainder of the power spectral density values accordingly.

5. The electronic system for heart rate detection according to claim 4, wherein the equivalent normalization value is one.

6. The electronic system for heart rate detection according to claim 2, wherein the heart rate detection module is further configured to:
　calculate a renormalization factor for the normalized power spectral density value set corresponding to the photoplethysmographic signal based on a ratio between: (i) a first value of the power spectral density value set corresponding to the photoplethysmographic signal at the frequency corresponding to the motion signal power spectral density peak value and (ii) a second value that is a maximum value of the power spectral density value set corresponding to the photoplethysmographic signal, which corresponds to a remainder of frequencies of interest.

7. The electronic system for heart rate detection according to claim 1, wherein the motion signal is a signal from an accelerometer or a gyroscope.

8. The electronic system for heart rate detection according to claim 1, wherein the first sensor circuit and the second sensor circuit of the random sampling sensor module are located in a single body part of a subject.

9. The electronic system for heart rate detection according to claim 1, wherein the frequency range of interest is 0.5 Hz to 5.0 Hz.

10. An electronic device comprising an electronic system for heart rate detection, wherein the electronic system for heart rate detection comprises:
   a random sampling sensor module comprising:
      a first sensor circuit configured to provide nonuniform random samples below a Nyquist rate of a photoplethysmographic signal; and
      a second sensor circuit configured to provide nonuniform random samples below a Nyquist rate of a motion signal, wherein the motion signal is sampled with an equivalent nonuniform pattern as the photoplethysmographic signal; and
   a heart rate detection module configured to:
      receive a plurality of the nonuniform random samples below the Nyquist rate of the photoplethysmographic signal;
      calculate a power spectral density value set based on a Lomb-Scargle periodogram of the nonuniform random samples below the Nyquist rate of the photoplethysmographic signal;
      receive a plurality of the nonuniform random samples below the Nyquist rate of the motion signal;
      calculate a power spectral density value set based on a Lomb-Scargle periodogram of the nonuniform random samples below the Nyquist rate of the motion signal;
      normalize the calculated power spectral density value sets corresponding to the photoplethysmographic signal and the motion signal;
      subtract the normalized power spectral density value set corresponding to the motion signal from the normalized power spectral density value set corresponding to the photoplethysmographic signal;
      renormalize the power spectral density value set corresponding to the photoplethysmographic signal; and
      calculate a heart rate value based on a frequency corresponding to a highest power peak value of the calculated power spectral density value set corresponding to the photoplethysmographic signal in a frequency range of interest.

11. The electronic device according to claim 10, wherein the heart rate detection module is further configured to:
   detect a motion signal power spectral density peak value and a frequency corresponding to the motion signal power spectral density peak value;
   normalize the power spectral density value set corresponding to the photoplethysmographic signal based on the motion signal power spectral density peak value; and
   normalize the power spectral density value set corresponding to the motion signal based on the motion signal power spectral density peak value.

12. The electronic device according to claim 11, wherein the motion signal power spectral density peak value is a maximum value in a frequency range of interest.

13. The electronic device according to claim 11, wherein the power spectral density value set corresponding to the photoplethysmographic signal and the power spectral density value set corresponding to the motion signal are normalized by setting a power spectral density value corresponding to the frequency of the motion signal power spectral density peak value to an equivalent normalization value and adapting a remainder of the power spectral density values accordingly.

14. The electronic device according to claim 13, wherein the equivalent normalization value is one.

15. The electronic device according to claim 11, wherein the heart rate detection module is further configured to:
   calculate a renormalization factor for the normalized power spectral density value set corresponding to the photoplethysmographic signal based on a ratio between: (i) a first value of the power spectral density value set corresponding to the photoplethysmographic signal at the frequency corresponding to the motion signal power spectral density peak value and (ii) a second value that is a maximum value of the power spectral density value set corresponding to the photoplethysmographic signal, which corresponds to a remainder of frequencies of interest.

16. The electronic device according to claim 10, wherein the motion signal is a signal from an accelerometer or a gyroscope.

17. The electronic device according to claim 10, wherein the first sensor circuit and the second sensor circuit of the random sampling sensor module are located in a single body part of a subject.

18. The electronic device according to claim 10, wherein the frequency range of interest is 0.5 Hz to 5.0 Hz.

19. A method for heart rate detection comprising:
   receiving a plurality of nonuniform random samples below a Nyquist rate of a photoplethysmographic signal;
   receiving a plurality of nonuniform random samples below a Nyquist rate of a motion signal, wherein the motion signal being is sampled with an equivalent nonuniform pattern as the photoplethysmographic signal;
   calculating a power spectral density value set based on a Lomb-Scargle periodogram of the plurality of nonuniform random samples below the Nyquist rate of the photoplethysmographic signal;
   calculating a power spectral density value set based on a Lomb-Scargle periodogram of the plurality of nonuniform random samples below the Nyquist rate of the motion signal;
   normalizing the calculated power spectral density value sets corresponding to the photoplethysmographic signal and the motion signal;
   subtracting the normalized power spectral density value set corresponding to the motion signal from the normalized power spectral density value set corresponding to the photoplethysmographic signal;
   renormalizing the power spectral density value set corresponding to the photoplethysmographic signal;
   detecting a frequency corresponding to the highest power peak value of the power spectral density value set corresponding to the photoplethysmographic signal in a frequency range of interest; and calculating a heart rate value based on the detected frequency.

20. The method of claim 19, wherein the method is performed by a processed executing instructions stored in a non-transitory, computer-readable storage medium.

* * * * *